United States Patent
Huber et al.

Patent Number: 5,521,319
Date of Patent: May 28, 1996

[54] BIOTINYLATION REAGENT AND METHOD OF USE THEREOF

[76] Inventors: Erasmus Huber, St. Willibald 10, D-86923 Finning; Bruno Zink, Seeblickstrasse 4, D-82449 Uffing; Helmut Lenz, Von-Kühlmann-Strasse 14, D-82327 Tutzing; Eva Hoess, Am Mühlberg 1a, D-82319 Starnberg, all of Germany

[21] Appl. No.: 295,793

[22] PCT Filed: Jan. 25, 1994

[86] PCT No.: PCT/EP94/00195

§ 371 Date: Sep. 14, 1994

§ 102(e) Date: Sep. 14, 1994

[87] PCT Pub. No.: WO94/17072

PCT Pub. Date: Aug. 4, 1994

[30] Foreign Application Priority Data

Jan. 27, 1993 [DE] Germany ............... 43 02 241.3

[51] Int. Cl.[6] .................................................. C07D 495/04
[52] U.S. Cl. ................................ 548/304.1; 548/315.1
[58] Field of Search .......................... 548/315.1, 304.1

[56] References Cited

FOREIGN PATENT DOCUMENTS

| | | |
|---|---|---|
| 0155854 | 9/1985 | European Pat. Off. . |
| 0156287 | 10/1985 | European Pat. Off. . |
| 0574000 | 6/1993 | European Pat. Off. . |
| 3629194A1 | 3/1987 | Germany . |
| WO94/17072 | 8/1994 | WIPO . |

OTHER PUBLICATIONS

Hofmann et al, Biochemistry, 1984, 23, 2547–2553.
Hoyer et al, J Am. Chem. Soc., 1990, 112 3249–3250.

*Primary Examiner*—David B. Springer

[57] ABSTRACT

The invention concerns a compound of the general formula (I):

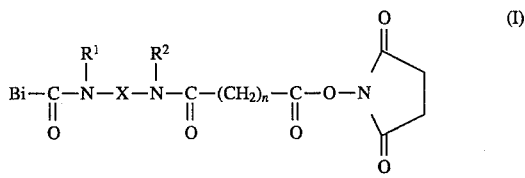

in which Bi denotes a residue derived by cleavage of a carboxyl group from biotin or from a biotin derivative, $R^1$ and $R^2$ denote independently of one another hydrogen or $C_1$–$C_4$ alkyl,
n denotes an integer from 4 to 10 and
X denotes an alkylene residue with a chain length of 5 to 20 atoms substituted by one or several O or/and S atoms and a conjugate of this compound with a substance that has at least one primary or/and secondary amino group $NHR^3$.

10 Claims, No Drawings

BIOTINYLATION REAGENT AND METHOD OF USE THEREOF

The present invention concerns a new biotinylation reagent, a process for its production, its use for biotinylating substances with free primary or/and secondary amino groups and a conjugate which is formed by reaction of the biotinylation reagent with substances containing amino groups. In addition the invention concerns a method for the determination of an analyte using the conjugate according to the invention as well as a reagent for the determination of an analyte that contains a conjugate according to the invention.

The binding pair comprising the binding partners biotin and streptavidin/avidin is of very great importance for methods in the field of medicine, biochemistry, molecular biology and immunology. The reason for this is that biotin or a biotin derivative that is bound to another substance is still capable of a high-affinity interaction with streptavidin or avidin and the biotin streptavidin/avidin complex formed in this manner represents an excellent detection system for biological substances.

Biotinylation of various substances such as proteins, peptides, nucleic acids, nucleotides or haptens using a biotinylation reagent has been known for a long time. Nowadays biotin active esters, in particular biotin-N-hydroxysuccinimide esters (biotin-NHS) (E. A. Bayer and M. Wilchek in Methods of Biochemical Analysis, Vol. 26 (Editor: D. Glick), Interscience Publication, J. Wiley & Sons, p. 2–45) and biotin-ε-amino-caproic acid-N-hydroxysuccinimide esters (biotin-X-NHS) (R. H. Burdon and P. H. von Knippenberg in Laboratory Techniques in Biochemistry and Molecular Biology, Vol. 15 (Editor: P. Tijssen), Elsevier, p. 23–38; S. M. Costello et al., Clin. Chem. 25/9 (1979), p. 1572–1580) are the most common biotinylation reagents.

Biotin when in the form of these active esters can be coupled via stable amide bonds to a reaction partner with primary or/and secondary amino functional groups without structurally impairing its heterobicycle moiety that is relevant for its binding capability to avidin/streptavidin. Since especially primary amino functional groups in the form of ε-amino groups of the lysine side chains occur in almost every protein, the aminolysis of the active esters has been established as the method of choice for biotinylating proteins such as antibodies or enzymatically active proteins and also haptens such as steroid hormones (L. X. Tiefenauer and R.

Y. Andres, J. Steroid Biochem. 35 (1990), p. 633–639). Therefore biotin-NHS and biotin-X-NHS are also sold by numerous manufacturers of fine chemicals and bioreagents.

It has also been known for a long time that in biotinylation reagents it has proven to be advantageous to introduce a spacer between the biotin unit and the reaction partner to be biotinylated (N. M. Green et al., Biochem. J. 125 (1971), p. 781–791). Spacers with amphiphilic structures have proven to be particularly useful for this (see e.g. EP 0 410 280 A1; EP 0 451 810 A1).

A disadvantage of the previously known biotin active esters is, however, that they are only sparingly soluble or in some cases even insoluble in almost all common organic solvents. For example biotin-NHS and in particular biotin-X-NHS are only moderately soluble in organic solvents with the exception of DMSO and DMF. The two aforementioned biotinylation reagents also exhibit only moderate solubility in water and aqueous buffer solutions. Although the commercially available biotinylation reagent sulfo-NHS-LC-biotin (I. M. Grumbach and R. W. Veh, J. Immunol. Meth. 140 (1991), p. 205–210) which is a sulfonated variant of biotin-X-NHS exhibits a good solubility in an aqueous medium, it is, however, on the other hand not soluble in organic solvents in the required concentrations. The latter has disadvantageous consequences in particular in the synthesis of hapten-biotin conjugates which is preferably carried out in organic solvents such as dioxane, DMF etc. (L. X. Tiefenauer and R. Y. Andres, J. Steroid Biochem. 35 (1990), p. 633–639; EP 0 451 810 A1).

The European Patent Application EP-A-0 156 287 describes a biotinylation reagent of the formula:

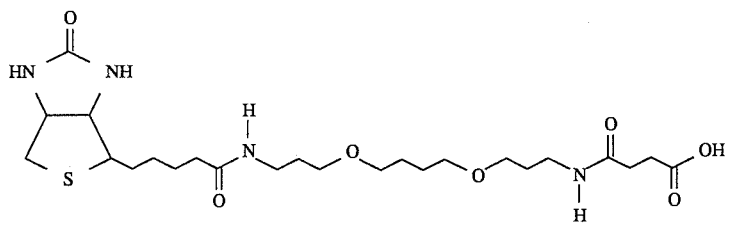

Biotin when in the form of these active esters can be coupled via stable amide bonds to a reaction partner with primary or/and secondary amino functional groups without structurally impairing its heterobicycle moiety that is relevant for its binding capability to avidin/streptavidin. Since especially primary amino functional groups in the form of ε-amino groups of the lysine side chains occur in almost every protein, the aminolysis of the active esters has been established as the method of choice for biotinylating proteins such as antibodies or enzymatically active proteins and also haptens such as steroid hormones (L. X. Tiefenauer and R.

This substance can be reacted with aminomethyltrioxalene hydrochloride at room temperature in the presence of a water-soluble carbodiimide for the production of a biotinylated psoralen derivative. It is mentioned on page 20, lines 23–25 of EP-A-0 156 287 that alternatively the carboxyl group of the above substance can be converted into an active ester such as N-hydroxysuccinimide and subsequently be reacted with aminomethyltrioxalen hydrochloride. Such a reaction is, however, not described in the form of an example since the substance formed by reaction of the above compound with N-hydroxysuccinimide having the formula:

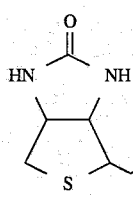
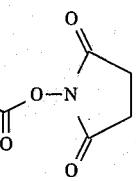

would be expected to decompose spontaneously in an intramolecular reaction with cleavage of hydroxysuccinimide and cyclization into the following substance due to the general instability of succinic acid-amide active esters:

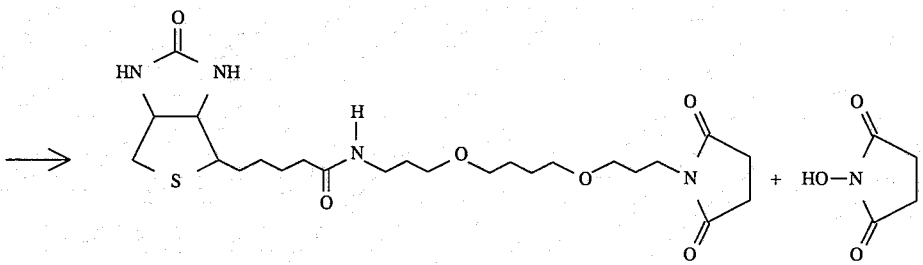

Thus no stable and isolatable biotin active esters are obtained according to the teaching of EP-A 0 156 287.

The object which is the basis of the present invention was therefore to provide a biotinylation reagent in which the aforementioned disadvantages of the state of the art are at least partially eliminated. In particular it is intended to provide a biotinylation reagent with a better solubility than previously known reagents.

The object according to the invention is achieved by a compound of the general formula I:

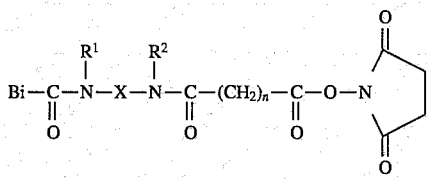

in which Bi denotes a residue derived by cleavage of a carboxyl group from biotin or from a biotin derivative, $R^1$ and $R^2$ denote independently of one another hydrogen or $C_1$–$C_4$ alkyl, n denotes an integer from 4 to 10 and X denotes an alkylene residue with a chain length of 5 to 20 atoms substituted by one or several O or/and S atoms.

Bi in formula I denotes a residue derived from biotin or from a biotin derivative by cleavage of a carboxyl group. Bi preferably denotes a residue derived from biotin, dethiobiotin, or iminobiotin and particularly preferably from biotin.

$R^1$ and $R^2$ denote independently of one another hydrogen or $C_1$–$C_4$-alkyl, $R^1$ and $R^2$ preferably denote hydrogen or methyl and particularly preferably hydrogen.

n denotes an integer from 4 to 10, particularly preferably an integer from 6 to 8.

X denotes an alkylene residue with a chain length of 5 to 20 atoms, preferably 5 to 11 atoms, substituted by one or several O or/and S atoms, preferably by one or several O atoms. X is preferably an unbranched residue but can also contain side groups such as methyl. The number of O or/and S atoms in the residue X is preferably 1–5, particularly preferably 1–3 and most preferably 2. In addition X preferably denotes a polyalkylene oxide derivative that for example contains butylene oxide ($C_4H_8O$—), propylene oxide ($C_3H_6O$—) and particularly preferably ethylene oxide ($C_2H_4O$—) units. X particularly preferably denotes a residue ($CH_2$—$CH_2O$)$_n$,$CH_2$—$CH_2$ in which n denotes an integer from 1 to 5, particularly preferably an integer from 1 to 3 and most preferably 2.

A most especially preferred subject matter of the present invention is biotinoyl-amino-3,6-dioxaoctanyl-aminocarbonyl-heptanoic acid-N-hydroxysuccinimide ester (biotin-DA-DOO-DSS or biotin-DDS) having the formula:

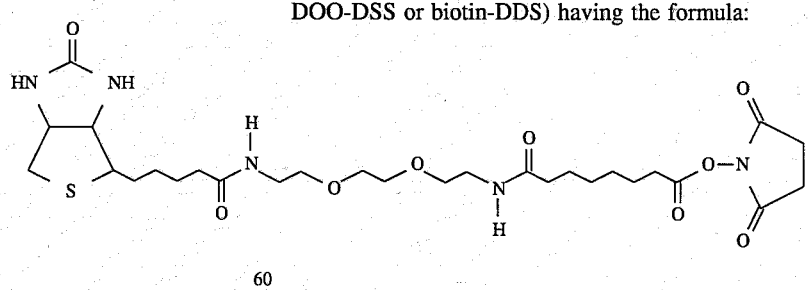

The compounds according to the invention are eminently suitable as biotinylation reagents since they enable biotin or biotin derivatives to be coupled in a one-step process without addition of further reagents to primary or/and secondary amino groups of reaction partners such as proteins, peptides, nucleic acids, nucleotides, haptens etc. The introduction of biotin groups in this process is achieved with a surprisingly high yield which was not previously possible with any other known reagent.

Furthermore the compounds according to the invention surprisingly have a substantially broader solubility spectrum in solvents such as water and organic solvents than the biotinylation reagents of the state of the art so that substances according to the invention can be used universally.

The present invention also concerns a process for the production of new biotinylation reagents which is characterized in that a compound of the general formula (II):

is reacted in an anhydrous aprotic solvent and in the presence of a base with a compound of the general formula (III):

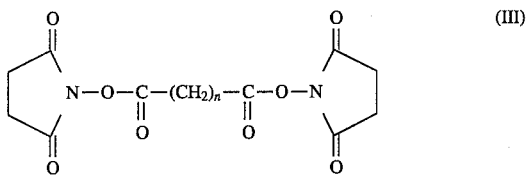

and the reaction product is isolated wherein Bi, $R^1$, $R^2$, X and n have the meanings stated in formula (I).

An example of a compound of formula (II) is the commercially available biotinoyl-1,8-diamino-3,6-dioxaoctane (biotin-DADOO, Boehringer Mannheim GmbH, Catalogue No. 1112047). An example of a compound of formula (III) is the commercially available disuccinimidyl suberate (DSS, Boehringer Mannheim GmbH, Catalogue No. 1081730). Reaction of these two substances forms the particularly preferred compound according to the invention biotin-DADOO-DSS.

The reaction is carried out in an anhydrous aprotic solvent, preferably DMF, in the presence of a base, preferably a tertiary amine (e.g. triethylamine) and preferably at room temperature. The product can be isolated from the reaction mixture by removing the solvent in a vacuum, digesting in water and filtering excess starting product. If necessary a further purification can be carried out by chromatography over silica gel.

The present invention in addition concerns the use of the new biotinylation reagents to biotinylate substances with free primary or/and secondary amino groups. Preferred examples of such substances are proteins such as antibodies (e.g. complete (monoclonal or polyclonal) antibodies or antibody fragments), enzymatically active proteins (e.g. peroxidase, β-galactosidase or alkaline phosphatase), nucleic acids (e.g. DNA, RNA, oligonucleotides), nucleotides (e.g. UTP, dUTP, ddUTP, ATP, dATP, ddATP) or haptens (e.g. fluorescein, steroid hormones such as estradiol, digoxigenin etc.) or peptides.

The present invention additionally concerns a conjugate of the general formula (IV):

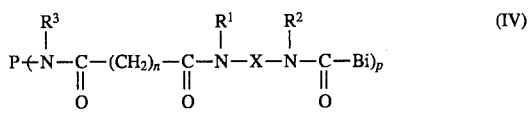

in which P denotes a substance that has at least one primary or/and secondary amino group $NHR^3$, $R^3$ denotes hydrogen or/and an alkyl residue which is substituted if desired, p denotes an integer of $\geq 1$ and
Bi, $R^1$, $R^2$, X and n are defined as in formula I.

The substance P is preferably a protein, a peptide, a nucleic acid, a nucleotide or a hapten, particularly preferably a protein such as an antibody or an enzymatically active protein. The symbol p corresponding to the degree of biotinylation of substance P denotes an integer $\geq 1$ and depends on the structure of the substance P i.e. on the number of reactive amino groups of the substance P. Thus p can denote 1 in the case of peptides or nucleotides that only have one free amino group whereas in the case of macromolecules such as proteins or nucleic acids p can denote a number of up to 100, preferably up to 20 and particularly preferably up to 10. In the case of an antibody a degree of biotinylation of for example 1:1 to 1:10 and in particular of 1:2 to 1:7.5 is preferred.

The invention also concerns a method for the determination of an analyte using a conjugate according to the invention. It is apparent that such methods can be carried out in a well-known manner and only differ from the methods of the state of the art in that new conjugates are used.

A surprising advantage of the use of the biotin conjugates according to the invention in a method for the determination of an analyte in comparison to conjugates of the state of the art is that in an electrochemiluminescence system and also in all other immunological tests in which spherical solid phases are used the conjugates produced with the new biotinylation reagent (biotin-DADOO-DSS) result in a performance that is 1.3-fold better than that obtained with biotin-X-NHS and about 3.5-fold better than that obtained with biotin-NHS.

Finally the invention also concerns a reagent for the determination of an analyte which contains a conjugate according to the invention. The reagent according to the invention is preferably in the form of a solution, a powder or a lyophilisate.

It is intended to further elucidate the invention by the following examples.

EXAMPLE 1

Synthesis of biotinoyl-amino-3,6-dioxaoctanylamino-carbonyl-heptanoic acid-N-hydroxysuccinimide ester (biotin-DADOO-DSS or biotin-DDS)

A solution of 561 mg (1.5 mmol) biotinoyl-1,8-diamino-3,6-dioxaoctane (biotin-DADOO, Boehringer Mannheim, Catalogue No. 1112074) in 25 ml freshly distilled dimethylformamide (DMF) is admixed with 0.21 ml (1.5 mmol) triethylamine and slowly added dropwise while stirring to a solution of 5.52 g (15 mmol) disuccinimidyl suberate (DSS, Boehringer Mannheim, Catalogue No. 1081730) in 50 ml freshly distilled DMF. It is allowed to stir for 18 hours at room temperature. Afterwards the solution is evaporated on a rotary evaporator in an oil pump vacuum, the semi-solid residue is digested with ca. 70 ml water and the excess DSS is separated by filtration. The clear solution is lyophilized and the lyophilisate is subsequently digested with a small amount of THF. After suction filtering the solid product it is dried in a high vacuum.

Yield: 620 mg colourless powder.

TLC: Silica gel 60 (Merck); ethyl acetate/glacial acetic acid/water 6/3/1 (v/v/v); spraying with a mixture of 1/1 (v/v) of A) 2% $H_2SO_4$ in ethanol and B) 0.2% 4-dimethylaminocinnamaldehyde in ethanol and subsequently drying for 10 minutes at 100° C. yields a raspberry-red spot of the product at $R_f$=0.51.

$^1$H-NMR($d_6$-DMSO): δ=1.10–1.80 (m, 14 H), 2.05 (t, 4H), 2.65 (t, 2H), 2.80 (s, 4H), 2.60–3.60 (m, 11H), 3.50 (s, 4H), 4.05–4.40 (m, 2 H), 6.36 (d, br, 2H), 7.80 (t, br, 2H).

EXAMPLE 2

Biotinylation of rabbit IgG 100 mg rabbit IgG is dissolved at a concentration of 5 mg/ml in PBS buffer pH 8.5 and admixed with a 10-fold molar amount of biotin-DSS in DMF (c=50 mg/ml). The solution is stirred for 1 hour at room temperature. Afterwards the reaction is stopped by addition of 10 ml 0.1 mol/l ammonium acetate solution. It is dialysed for 16 hours against PBS buffer pH 7.5 and subsequently lyophilized.

EXAMPLE 3

Solubility of biotinylation reagents

| | Solubility in mg/ml at 20° C. | | | |
|---|---|---|---|---|
| | water | DMF | methanol | dichloromethane |
| biotin-DDS | 7 | 20 | 20 | 10 |
| NHS-LC-biotin | 2 | 20 | 20 | <1 |
| biotin-X-NHS | 10 | 10 | 10 | <1 |

NHS-LC-biotin: Pierce No. 21335
biotin-X-NHS: biotinoyl-aminocaproic acid-N-hydroxysuccinimide ester, Boehringer Mannheim No. 1003933

The results of the solubility experiments on biotin-DA-DOO-DSS compared with biotinylation reagents of the state of the art show that the biotinylation reagent according to the invention has a considerably broader solubility spectrum than known compounds. Above all it exhibits a good solubility in strongly polar (water) as well as in non-polar (dichloromethane) solvents.

EXAMPLE 4

Biotinylation of monoclonal antibodies against thyrotropin (TSH)

The monoclonal antibody anti-TSH M 1.20 (MAB <hTSH>M-I 20PK30, ECACC 87122202) is dissolved in 0.1 mol/l potassium phosphate buffer pH 8.4 at a concentration of 10 mg/ml. After addition of the 3.5-fold or 8-fold molar amount of biotin-DDS (or for comparison biotin-X-NHS or biotin-NHS, dissolved in dimethylsulfoxide at a concentration of 9.5 mg/ml in each case) it is stirred for 90 minutes at 25° C. and the reaction is subsequently stopped by addition of 10 µl mol/l lysine. After dialysis against 25 mmol/l potassium phosphate/50 mmol/l sodium chloride pH 7.0, the product is lyophilized.

EXAMPLE 5

Immunological determination of TSH and hepatitis B surface antigen (HBs) by means of electrochemiluminescence a) Production of ruthenium-labelled F(ab')$_2$ fragments In the electrochemiluminescence determination TSH and HBs are detected by means of ruthenium-labelled antibody fragments against TSH or HBs. In order to prepare these fragments, 100 mg of the monoclonal antibody anti-<TSH>-M-A8 (Boehringer Mannheim GmbH, Cat. No. 1367978) or anti-<HBs>-M-5A10 (Boehringer Mannheim GmbH, Catalogue No. 112 4986-122) are cleaved with pepsin according to Johnstone and Thorpe (Immunochemistry in Practice, p. 61, Blackwell Scientific, 1987) and the resulting F(ab')$_2$ fragments are purified by chromatography on Sepharose S 200 HR (Pharmacia LKB). In each case 5 mg of these purified fragments is dissolved in 1 ml 0.15 mol/l potassium phosphate buffer/0.15 mol/l sodium chloride pH 7.8. Immediately before use 5 mg Ru(bpy)$_3^{2+}$-NHS (ruthenium (2,2'-bipyridyl)$_2$(4-[3-(N-hydroxysuccinimidylcarboxy)-propyl]-4'-methyl-2,2'-bipyridine)$^{2+}$) (prepared according to EP-A 0 265 519) is dissolved in 0.75 ml anhydrous dimethylsulfoxide. This active ester is added by pipette in a molar ratio of 7.5:1 of ester to F(ab')$_2$ fragment (corresponding to 0.396 mg Ru(bpy)$_3^{2+2+}$-NHS/5 mg F(ab')$_2$) while stirring. Subsequently it is incubated for 60 minutes at 25° C. and the reaction is stopped by addition of 10 µl mol/l lysine. After dialysis against 25 mmol/l potassium phosphate buffer/0.1 mol/l sodium chloride pH 7.0 for 24 hours, the product is lyophilized.

b) Procedure for the electrochemiluminescence measurement

The biotinylated antibodies anti<TSH>M 1.20 obtained according to example 4 as well as the antibody against the hepatitis B surface antigen anti<HBs>M-5A10 prepared in an analogous manner are dissolved at a concentration of 2.25 µg/ml in incubation buffer that contains 20% rabbit serum.

Incubation buffer:

112 mmol/l KH$_2$PO$_4$ 88 mmol/l K$_2$HPO$_4$ 0.05 mmol/l sodium chloride 6.5 mmol/l NaN$_3$ 0.8 µmol/l Triton X-100

0.4 mmol/l Tween 20

100 mmol/l tripropylamine dissolved in water (pH 7.55–7.65).

The ruthenium-labelled F(ab')$_2$ fragments of the monoclonal antibody anti<TSH>M-A8 or anti<HBs>M-5A10 are dissolved at a concentration of 1 µg/ml in incubation buffer containing 20% rabbit serum additive. Streptavidin magnetic particles (superparamagnetic polystyrene particles of 2.8 µm diameter, Dynal A. S., Oslo, Norway) are suspended at a concentration of 600 µg/ml incubation buffer/20% rabbit serum and kept in homogeneous dispersion by shaking. The following are pipetted into each polystyrene tube for the electrochemiluminescence measurement:

50 µl magnetic particle suspension

50 µl biotinylated antibodies

50 µl ruthenium-labelled (Fab')$_2$ fragments

50 µl TSH standard solution (60 µU/ml) or HBsAg standard solution 12 units/ml, Boehringer Mannheim GmbH, Catalogue No. 112 4986-122)

The tubes are incubated for 16 minutes at room temperature while shaking. Subsequently 500 µl incubation buffer is added and after mixing an aliquot of 225 µl of the ruthenium-label bound to the magnetic particles is determined with the electrochemiluminescence measuring instrument Origen 1.0 from the Igen Inc., Company, Rockville, USA (see also G. F. Blackburn et al., Clinical Chemistry 37 (1991), 1534). The result of these measurements is shown in the following table.

| Biotinylated antibody | Degree of biotinylation | Signal |
|---|---|---|
| MAB<TSH>M 1.20-IgG-Bi (DDS)* | 1:3.5 | 130 724 |
| MAB<TSH>M 1.20-IgG-Bi (X-NHS) | 1:3.5 | 103 965 |
| MAB<TSH>M 1.20-IgG-Bi (NHS) | 1:3.5 | 37 300 |
| MAB<TSH>M 1.20-IgG-Bi (DDS)* | 1:8 | 86 600 |
| MAB<TSH>M 1.20-IgG-Bi (X-NHS) | 1:8 | 86 100 |
| MAB<TSH>M 1.20-IgG-Bi (NHS) | 1:8 | 54 950 |
| MAB<HBs>M-5A10-IgG-Bi (DDS)* | 1:7.5 | 160 842 |
| MAB<HBs>M-5A10-IgG-Bi (X-NHS) | 1:7.5 | 121 994 |

*Example according to the invention

The data show that considerably higher signals are obtained in the electrochemiluminescence measurement using antibodies biotinylated with biotin-DDS or biotin-X-NHS than with biotinylation with the spacer-free biotin-NHS. A lower degree of biotinylation results in higher signals in each case. In this experiment a signal yield that is a further 25.7% higher is obtained with the antibodies biotinylated via biotin-DDS than with the antibodies biotinylated via biotin-X-NHS. A signal optimum at a low degree of biotinylation is preferable since the surface properties of the biotinylated antibody are changed less than is the case with a higher degree of biotinylation.

EXAMPLE 6

Immunological determination of TSH using streptavidin magnetic particles and photometric signal measurement.

The TSH test is carried out for the photometric measurement using anti-TSH-M-A8 Fab fragments that are coupled to peroxidase (POD). This conjugate as well as TSH standard, washing solution and ABTS substrate are taken from an Enzymun TSH test kit (Boehringer Mannheim GmbH, Catalogue No. 1488635).

Procedure for the test:

The antibodies anti-TSH-M-1.20 biotinylated according to example 4 are dissolved at a concentration of 3 µg/ml in incubation buffer.

| Incubation buffer: (weight specification per 1 l) | |
|---|---|
| $NaH_2PO_4$ | 2.5 g |
| $Na_2HPO_4$ | 12.8 g |
| Di—Na tartrate | 46 g |
| Synperonic F 68 | 5 g |
| bovine IgG | 1 g |
| bovine albumin | 1 g |
| phenol | 0.1 g |

The pH value is adjusted with NaOH to 7.4.

The concentrate of the enzyme conjugate MAB<TSH>M-A 8-Fab-POD from the Enzymun TSH test kit is diluted 1:50 in incubation buffer.

Streptavidin magnetic particles (Dynabeads M 280) are suspended in incubation buffer at a concentration of 600 µg/ml and kept in homogeneous dispersion by shaking.

Wells of a microtitre plate (Nunc Maxi Sorp) are incubated for 1 hour at room temperature with a 1% solution of Crotein C in 50 mM HEPES buffer/0.15M NaCl, pH 7.9 to saturate adsorptive binding sites.

After aspirating the solution, the following are pipetted into the wells:

50 µl magnetic particle suspension
50 µl conjugate solution MAB-A8-POD
50 µl biotinylated antibody
50 µl TSH standard solution (40 µU)

The reaction mixtures are incubated for 45 minutes at room temperature while shaking.

Subsequently the magnetic particles of each well are collected at the bottom using a suitable magnet, the supernatant in each case is decanted and 0.3 ml washing solution is pipetted in each case onto the particles with the magnet removed.

After again collecting the particles with the magnet, the washing solutions are poured away. The washing procedure is repeated twice.

At the end of the third wash, 0.2 ml ABTS substrate solution is added to each well and incubated at room temperature while shaking.

After 16 min the colour absorbance at 405 nm in the wells is measured in a photometer for microtitre plates.

The result of these measurements is shown in the following table.

| Biotinylated antibody | Degree of biotinylation | Absorbance at 405 nm |
|---|---|---|
| MAB<TSH>M-1.20-IgG-Bi (DDS) | 1:3.5 | 1.484 |
| MAB<TSH>M-1.20-IgG-Bi (X-NHS) | 1:3.5 | 1.225 |
| MAB<TSH>M-1.20-IgG-Bi (DDS) | 1:8 | 1.400 |
| MAB<TSH>M-1.20-IgG-Bi (X-NHS) | 1:8 | 1.291 |

The data show that significantly higher signals result in a magnetic particle immunological test with an antibody-POD conjugate even when measured photometrically using biotin-DDS labelled antibody compared to an antibody which is biotinylated with biotin-X-NHS. Biotin-DDS also again yields a signal optimum at a lower degree of biotinylation.

We claim:

1. Compound of the general formula (I):

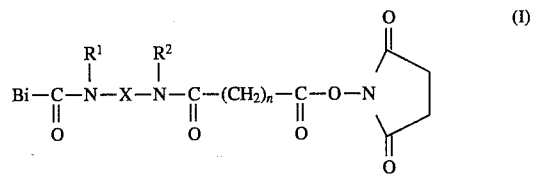

in which Bi denotes a residue derived by cleavage of a carboxyl group from biotin or from a biotin derivative, $R^1$ and $R^2$ denote independently of one another hydrogen or $C_1$—$C_4$ alkyl, n denotes an integer from 4 to 10 and X denotes an alkylene residue with a chain length of 5 to 20 atoms substituted by one or several O or/and S atoms.

2. Compound as claimed in claim 1, wherein

Bi denotes a residue derived from biotin, dethiobiotin or iminobiotin.

3. Compound as claimed in claim 1 or 2, wherein $R^1$ and $R^2$ denote hydrogen.

4. Compound as claimed in one of the claim 1, wherein n denotes an integer from 6 to 8.

5. Compound as claimed in one of the claim 1, wherein

X represents an alkyl residue substituted by one or several O atoms.

6. Compound as claimed in one of the claim 1, wherein

X represents a residue $(CH_2—CH_2O)_m CH_2—CH_2$ in which m denotes an integer from 1 to 5.

7. Compound as claimed in one of the claim 1, wherein

X denotes a residue with a chain length of 5 to 11 atoms.

8. Biotinoyl-amino-3,6-dioxaoctanyl-aminocarbonyl-heptanoic acid-N-hydroxysuccinimide ester.

9. Process for the production of a compound as claimed in one of the claim 1, wherein a compound of the general formula (II):

is reacted in an anhydrous aprotic solvent and in the presence of a base with a compound of the general formula (III):

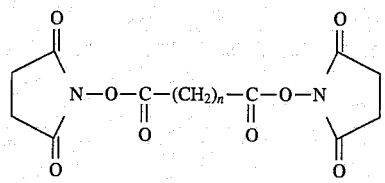 (III)

and the reaction product is isolated, in which Bi, $R^1$, $R^2$, X and n have the meanings stated in claim 1.

10. A method of using the compound of claim 1 for biotinylating a substance with free primary or secondary amino groups, consisting essentially of bringing said compound into contact with said amino group containing substance, with or without slight warming, to effect the formation

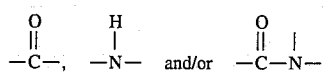

groups by elimination of the

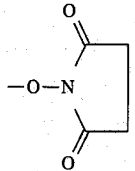

moiety.

* * * * *

UNITED STATES PATENT AND TRADEMARK OFFICE
CERTIFICATE OF CORRECTION

PATENT NO. : 5,521,319
DATED : HUBER et al.
INVENTOR(S) : February 7, 1997

It is certified that error appears in the above-indentified patent and that said Letters Patent is hereby corrected as shown below:

On the Title page, please add item [73] Assignee: below item [76]:
Assignment should read --Boehringer Mannheim GmbH, Mannheim, Germany--.

Signed and Sealed this

Fifteenth Day of April, 1997

Attest:

BRUCE LEHMAN

Attesting Officer         Commissioner of Patents and Trademarks